(12) United States Patent
Crisanti et al.

(10) Patent No.: US 7,611,669 B1
(45) Date of Patent: Nov. 3, 2009

(54) ASSAY DEVICE

(75) Inventors: Andrea Crisanti, London (GB); Uri Friedlander, London (GB); Tito Bacarese-Hamilton, Surrey (GB)

(73) Assignee: Imperial College Innovations Ltd., London (GB)

( * ) Notice: Subject to any disclaimer, the term of this patent is extended or adjusted under 35 U.S.C. 154(b) by 431 days.

(21) Appl. No.: 10/181,620

(22) PCT Filed: Oct. 13, 2000

(86) PCT No.: PCT/GB00/03949

§ 371 (c)(1), (2), (4) Date: Feb. 24, 2003

(87) PCT Pub. No.: WO01/27627

PCT Pub. Date: Apr. 19, 2001

(30) Foreign Application Priority Data

Oct. 14, 1999 (GB) .................................. 9924222.4

(51) Int. Cl.
*G01N 21/00* (2006.01)
*G01N 1/10* (2006.01)
*G01N 21/49* (2006.01)
*G01N 33/543* (2006.01)

(52) U.S. Cl. ................... 422/57; 436/180; 436/518; 250/576

(58) Field of Classification Search ............ 422/57, 422/55, 56, 58, 101; 435/7, 805, 810; 436/512, 436/180, 518; 250/576
See application file for complete search history.

(56) References Cited

U.S. PATENT DOCUMENTS

| | | | |
|---|---|---|---|
| D288,716 S | 3/1987 | Covell et al. | |
| 4,883,760 A | 11/1989 | Heelies | |
| 4,943,522 A | 7/1990 | Eisinger et al. | |
| 5,137,691 A | 8/1992 | Parker | |
| 5,137,827 A * | 8/1992 | Mroczkowski et al. | ... 435/287.2 |
| 5,256,372 A | 10/1993 | Brooks et al. | |
| 5,656,502 A * | 8/1997 | MacKay et al. | ............. 436/180 |
| 5,656,503 A | 8/1997 | May et al. | |
| 5,770,460 A | 6/1998 | Pawlak et al. | |
| 6,140,136 A * | 10/2000 | Lee | ............................ 436/518 |
| 6,239,445 B1 * | 5/2001 | Shaeef | ....................... 250/576 |

FOREIGN PATENT DOCUMENTS

| WO | WO 93/18398 | 9/1993 | |
|---|---|---|---|
| WO | WO9800712 | * | 1/1998 |

OTHER PUBLICATIONS

Extract from Sigma Catalogue.

* cited by examiner

*Primary Examiner*—Jill Warden
*Assistant Examiner*—Lore Jarrett
(74) *Attorney, Agent, or Firm*—Nikolai & Mersereau, P.A.; C. G. Mersereau (57) ABSTRACT

The invention provides an assay device for quantification or detection of the presence or absence of an analyte in a liquid sample, comprising a molding (1) permanently or removably attached to a substantially planar plate (2) such that a part of said molding forms a capillary chamber (3) between said plate and the said molding, the device further comprising a chamber (5) into which a test sample and/or reagent can be introduced and further comprising a chamber (7) capable of accommodating an absorbent pad, wherein the said chamber into which a test sample and said chamber capable of holding an absorbent pad are in lateral flow contact via the said capillary chamber (3).

19 Claims, 8 Drawing Sheets

BEFORE MOULDINGS HAVE BEEN PUSHED ALONG EACH OTHER, A GAP IS PRESENT BETWEEN THE ABSORBING PAD AND THE CAPILLARY GAP

AFTER BOTH MOULDINGS HAVE BEEN PUSHED TOGETHER, AN INTIMATE CONTACT IS ACHIEVED BETWEEN ABSORBING PAD AND CAPILLARY GAP

| | IF ANTIGEN IS THERE | IF THERE IS NO ANTIGEN |
|---|---|---|
| SANDWICH ASSAY | ANTIGEN LINKS THE LABELLED ANTIBODY ONTO A SOLID MATERIAL | IF NO ANTIGEN PRESENT, THE LABEL IS NOT BOUND TO THE SOLID SUPPORT |
| COMPETITIVE ASSAY | ANTIGEN BINDS TO THE ANTIBODY IN SOLUTION | IF NO ANTIGEN IS PRESENT, THEN THE ANTIBODY IS FREE TO BIND ONTO THE SOLID SUPPORT |

| TYPE OF ASSAY | WHEN ANTIGEN IS PRESENT | WHEN ANTIGEN IS ABSENT |
|---|---|---|
| LATEX AGGLUTINATION ASSAY | MICROSPHERES HELD TOGETHER BY ANTIGEN — LATEX FORMS CLUMPS | MICROSPHERES NOT HELD TOGETHER — LATEX FORMS UNIFORM SUSPENSION |

*Fig. 1*

Fig. 1
(Page 2 of 2)

ASSAY DEVICE

BACKGROUND OF THE INVENTION

I. Field of the Invention

The present invention relates to a device suitable for use in performing assays, for example immunological and related assays.

II. Related Art

Assays, for example on biological samples, may be binding assays, for example sandwich or competitive binding assays. Binding assays may make use of immunological interactions. Such assays are known as immunoassays and make use of the high specificity and high affinity of the interaction between an antibody or other immunoglobulin-type molecule and its target antigen.

Binding assays, for example immunoassays, may be useful in medical diagnoses. Diagnostic tests using such assays may be carried out in a laboratory, medical practitioner's surgery or hospital or in a home setting, either by the patient or by a visiting medical practitioner. Devices suitable for carrying out diagnostic tests, particularly those intended for use by non-medically trained personnel, for example patients, may be designed to give a visible test result. These may comprise a support, for example of nitrocellulose, on which an interaction may take place in order to provide the visible test result. Other devices suitable for carrying out diagnostic tests may comprise a capillary test chamber formed between a plastic moulding and a microscope glass slide. These may require a microscope or other instrument in order to determine the test result.

Assays may make use of a lateral flow protocol, for example in which a bibulous or non-bibulous material conducts liquid from one portion of the device to another. Examples of diagnostic test devices using assays, particularly those making use of a lateral flow protocol, are described and reviewed, for example, in U.S. Pat. No. 5,770,460 and in U.S. Pat. No. 4,943,522. As set out in U.S. Pat. No. 4,943,522, a bibulous material may be capable of adsorbing or "imbibing" one or more dissolved or dispersed components of a liquid sample, whereas a non-bibulous material may not so adsorb such components, such that all dissolved or dispersed components of the liquid are carried at substantially equal rates and with relatively unimpaired flow laterally through the membrane. Examples of bibulous materials may include untreated paper, nitrocellulose or nylon and other materials that may be used in chromatographic separation techniques.

The apparatus disclosed in U.S. Pat. No. 4,943,522 comprises a non-bibulous lateral flow membrane which has on its surface a sample application zone and at a lateral distance from the application zone, at least one indicator zone. The membrane may be bound between two sheets.

A further example of an apparatus suitable for performing immunoassays is described in U.S. Pat. No. 4,883,760. This makes use of capillary tubes and a flexible support that enables the end of the capillary tube to be brought into contact with an absorbent material by the application of moderate manual pressure on the support. However, such an apparatus is bulky and suitable only for producing a test result which is assessed by eye.

Known test devices, for example as summarised in the documents cited above, may have disadvantages in terms of convenience or of flexibility or accuracy in performing complex assays. Thus, there is a need for a compact device that allows complex assays, for example those requiring timed incubation or washing steps, to be performed reproducibly. It is an object of the invention to provide an improved assay device.

SUMMARY OF THE INVENTION

The invention provides an assay device for quantification or detection of the presence or absence of an analyte in a liquid sample, comprising:

a first portion;

a lateral flow zone;

a sample receiving zone in the first portion in contact with the lateral flow zone; and a second portion having means for holding an absorbent pad, wherein the first portion is arranged in sliding relation to the second portion such that the second portion is movable between a first position in which there is a gap between an absorbent pad held by the second portion and the lateral flow zone and a second position in which an absorbent pad held by the second portion is in intimate contact with the lateral flow zone.

It will be appreciated that a device according to the invention may be useful in performing an assay in which binding of at least a portion of the analyte to a specific binding partner for the analyte is detected.

It is preferred that the lateral flow zone comprises a capillary chamber. Lateral flow through the capillary chamber may occur when liquid is introduced into the sample receiving zone. Alternatively, the lateral flow zone may comprise a solid support through which lateral flow may occur when liquid is introduced into the sample receiving zone.

The lateral flow zone may form or comprise a binding and/or detection zone. The detection zone may be suitable for binding to occur between at least a portion of the analyte and a specific binding partner for said analyte, and to be detected. The binding zone may be suitable for binding of at least a portion of the analyte to a specific binding partner for said analyte to occur; however, it may not be suitable for such binding to be detected. The binding and/or detection zone comprises a capture reagent, as discussed further below. It will be appreciated that the binding zone may be suitable for detection of such binding if the device is disassembled. It is preferred that the lateral flow zone may form or comprise a detection zone.

It is preferred that the device comprises a substantially planar plate. It is further preferred that the substantially planar plate forms a wall of or support for the lateral flow zone. It is particularly preferred that the substantially planar plate forms a wall of a capillary chamber comprised in the lateral flow zone.

It is preferred that lateral flow through the lateral flow zone is substantially planar.

It is preferred that the detection and/or binding zone is substantially planar. As discussed further below, more than one species of capture reagent may be immobilised in the detection or binding zone; it is preferred that all such capture reagents are immobilised in substantially the same plane, still more preferably substantially parallel to the said substantially planar plate. It is further preferred that the capture reagents may be immobilised on the surface of the said planar plate that forms a wall of the capillary chamber. This may aid detection of binding to each said capture reagent, particularly when using an automated detection system.

The device may comprise an absorbent pad held by the second portion. The means for holding the absorbent pad may comprise means arranged to grip the absorbent pad, for example a push-fit arrangement. Alternatively, the means may comprise a part of the portion to which the pad may be glued, for example using a suitable adhesive, as well known to those skilled in the art.

It is preferred that all dissolved or dispersed components of said assay or binding reaction (with the exception of the analyte or reagent binding to the specific binding partner, as appropriate) flow through the device to the absorbent zone at substantially equal rates. Thus, in the terminology summarised above, it is preferred that the lateral flow is non-bibulous lateral flow. However, it will be appreciated that the lateral flow may be bibulous flow.

Such non-bibulous flow may occur if the lateral flow occurs through a capillary chamber, particularly if the walls of the chamber are formed of glass or a material, for example a plastics material, which is wettable by water ie has a contact angle of less than 90° with water, as known to those skilled in the art and as discussed further below. Suitable plastics materials are polycarbonate and styrene-acrylonitrile polymer (SAN). It is preferred that the lateral flow occurs through a capillary chamber. It will be appreciated that in such an embodiment there is no requirement for a solid support through which lateral flow can occur.

Thus, the device may comprise a capillary chamber, preferably a substantially planar capillary chamber. It is preferred that lateral flow through the lateral flow zone occurs through the said capillary chamber. The capillary chamber may comprise the detection and/or binding zone. Preferably, the detection and/or binding zone does not extend beyond the boundaries of the capillary chamber.

The capillary chamber may be formed by the first portion in cooperation with the substantially planar plate. The first portion may form a capillary chamber when placed directly in contact with the said substantially planar plate. However, it will be appreciated that a spacer, which may be in the form of a frame-like structure, may be required between the said planar plate and the first portion in order to form the capillary chamber.

The capillary chamber may have a depth (for example distance between the substantially planar plate and the part of the said portion that forms the face of the capillary chamber that is substantially parallel to the plane of the said plate) of between about 0.01 mm and 2 mm, preferably between 0.01 mm and 1 mm, still more preferably between 0.05 and 1 mm, yet more preferably between about 0.1 and 0.5 mm.

It will be appreciated that the depth should be such that liquid placed at the edge of the capillary chamber in the sample-receiving zone flows across the entire capillary chamber. It is preferred that the liquid that enters the capillary chamber substantially all flows into the absorbent pad when (but only when) the absorbent pad is in lateral flow contact with the capillary chamber ie with an edge of the capillary chamber. When there is a gap between the absorbent pad and the lateral flow zone, it will be appreciated that liquid does not flow from the lateral flow zone into the absorbent pad. It will be appreciated that the required depth may depend upon the edge-to-edge length of the capillary chamber, the viscocity of the liquid and contact angle of the liquid to be tested on the surfaces of the capillary chamber (which depends on both the surface tension of the liquid and the nature of the surfaces). It will be appreciated that the appropriate depth may be readily determined for a particular combination of parameters, for example by the use of spacers of different thicknesses to form chambers of different depths. Factors affecting capillarity are discussed, for example, in Remington: The Science and Practice of Pharmacy, 19$^{th}$ Ed, Mack Publishing Company 1995, particularly in Chapter 19 of Volume 1.

The depth of the capillary chamber may not be constant over the area of the capillary chamber. For example, it may be advantageous for the depth of the chamber to be greater at the edge of the capillary chamber adjacent to/in contact with the sample-receiving zone than at the edge of the capillary chamber that comes into contact with the absorbent pad. Thus, the depth of the chamber may decrease substantially evenly from the edge of the capillary chamber adjacent to the sample-receiving zone to the edge of the capillary chamber that comes into contact with the absorbent pad. This may aid the flow of liquid through the capillary chamber. It may make formation of bubbles in the capillary chamber less likely to occur and may aid even flow of liquid across the width of the capillary chamber.

Figure 7:
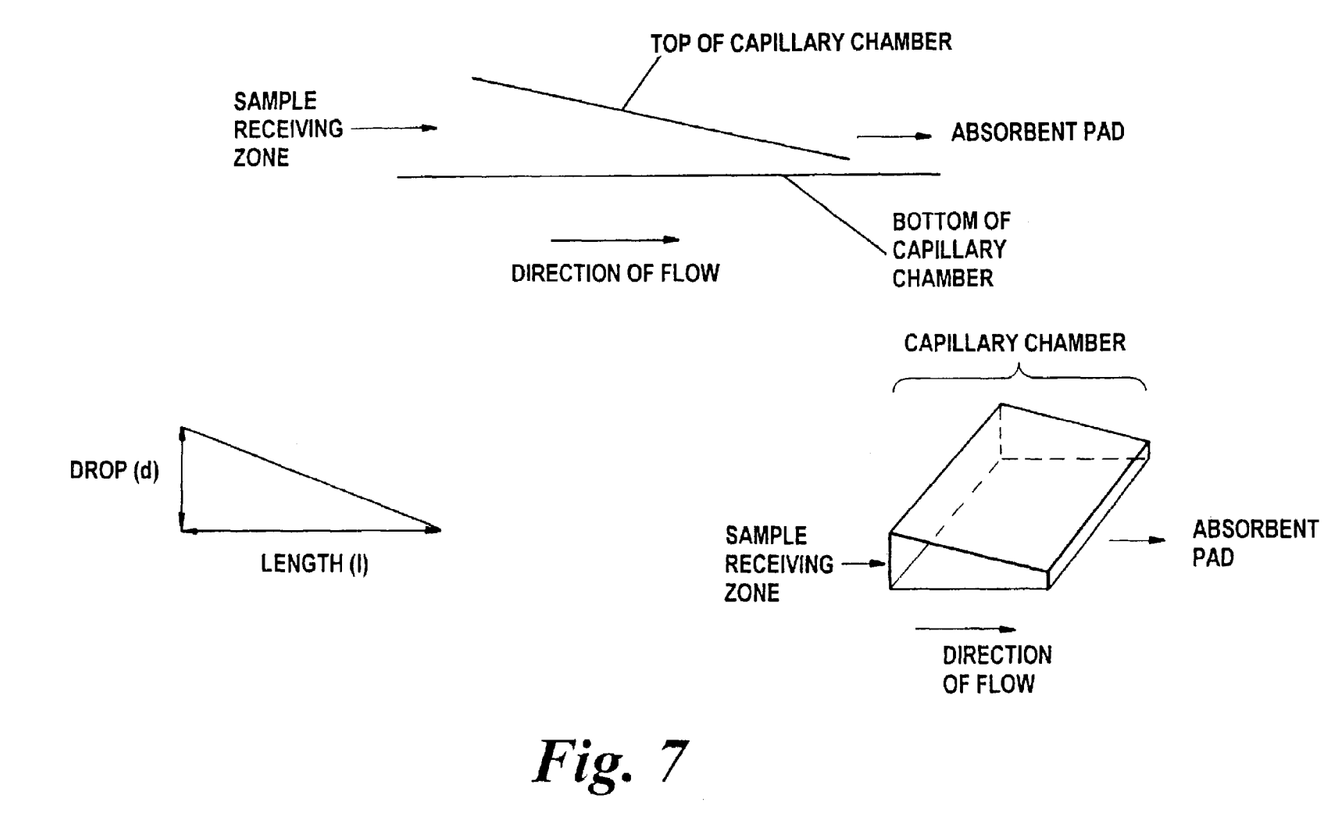
FIG. 7 illustrates the principles of a sloping capillary chamber (side view and perspective view).

The change in depth may preferably be achieved by a slope in the part of the said portion that forms a face of the capillary chamber (formed in cooperation with the substantially planar plate). It will be appreciated that the choice of slope may require a compromise. An increase in the degree of slope may improve the flow of liquid through the capillary chamber but also increases the volume of the capillary chamber (for a given depth at the edge of the capillary chamber that comes into contact with the absorbent pad) and hence the volumes of reagents required. The slope may be preferably be between about 0.1% and 5%, still more preferably between about 1% and 3%, most preferably about 2% (expressed as drop (d) as a percentage of length (l), as shown in FIG. 7).

The preferred depth at the edge of the capillary chamber that comes into contact with the absorbent pad is between about 0.01 mm and 2 mm, preferably between 0.01 mm and 1 mm, still more preferably between 0.05 and 1 mm, yet more preferably between about 0.1 and 0.5 mm. It will be appreciated that the first portion may comprise a part for forming a wall of the capillary chamber that is made of or coated with a material different to other parts of the first portion. For example, water does not wet polyethylene effectively and thus a polyethylene surface may be less desirable than a more polar surface, for example a glass surface. It will be appreciated that the use of a wetting agent in the liquid sample or on the surfaces of the capillary chamber may be beneficial.

It is preferred that the edge-to-edge length of the capillary chamber is preferably between 1 and 70 mm, still more preferably between about 5 and 25 mm.

It is preferred that at least a portion of the said substantially planar plate is transparent to visible, UV and/or infra-red radiation. It is further preferred that the said portion of the substantially planar plate that is transparent comprises a portion that forms a wall of the said capillary chamber. It will be appreciated that this may be desirable to allow detection of any binding to the capture reagent in the capillary chamber. Alternatively, at least a portion of a wall of the said planar capillary chamber is transparent to visible, UV and/or infra-red radiation.

It is preferred that the plate surface which forms the capillary chamber is glass.

If the device comprises a solid support through which the lateral flow occurs, then it is preferred that the said solid support is of a non-bibulous ie non-chromatographic material. As described in U.S. Pat. No. 5,770,460, bibulous materials (for example paper or nitrocellulose) may be converted to materials that exhibit nonbibulous flow characteristics by the application of blocking agents, in particular certain detergents and proteins, which serve to obscure the interactive forces that may account for the bibulous nature of the supports prior to treatment.

A solid support which supports lateral flow may be in the form of a membrane. The membrane may have a much smaller thickness than surface dimension and is hydrophilic enough to be wetted and thus permit aqueous solutions and suspensions to exhibit lateral flow freely, and preferably isotropically, preferably at substantially the same rates for various components of a sample.

Intrinsically non-bibulous materials include porous polyethylene sheets, for example the high density or ultra high molecular weight polyethylene sheet material manufactured by Porex Technologies Corp. of Fairburn, Ga., USA, as described, for example in U.S. Pat. No. 4,943,522. This membrane has an open pore structure with a typical density, at 40% void volume, of 0.57 gm/cc (0.57 g/ml) and an average pore diameter of 1 to 250 μm, generally being from 3 to 100 μm. The optimum pore diameter for the membrane for use in the device of the invention may be from about 10 to 50 μm. The membranes are from about 0.0025 cm (0.025 mm) to about 0.5 cm (5 mm) thick, typically in the range 0.012 cm to 0.025 cm (0.25 mm). The membrane may be backed with a generally water impervious layer or may be self-supporting. Other membranes that may be suitable include membranes formed from other olefin or other thermoplastic materials, for example polyvinyl chloride, polyvinyl acetate, copolymers of vinyl acetate and vinyl chloride, polyamide, polycarbonate or polystyrene.

The properties of suitable membranes will be well known to those skilled in the art, and as summarised, for example, in U.S. Pat. No. 4,943,522. Thus, suitable membranes may have pore sizes between about 3 to 100 μm, preferably about 10-50 μm, be less than 0.5 cm thick and be constructed of an inert material. The membrane is capable of supporting lateral flow, preferably non-bibulous flow ie non-chromatographic flow, and preferably isotropic flow. The lateral flow may occur by a mechanism involving capillary action.

Blocking agents that may be used to convert a bibulous material to one exhibiting non-bibulous flow include, as known to those skilled in the art and described in U.S. Pat. No. 5,770,460, bovine serum albumin (which may be methylated or succinylated), whole animal sera or other blood proteins, casein and non-fat dry milk. Detergent-based blocking agents may also be used, either alone or in combination with a protein-based blocking agent. Suitable detergents may include polyoxyethylene sorbitan alcohol detergents (Tween detergents), polyoxyethylene alcohols (eg Nonidet P-40) or polyoxyethylene ethers (eg Triton X-100). Methods and considerations concerning such treatments of bibulous materials are described in U.S. Pat. No. 5,770,460. The advantage of using a treated bibulous material as the support material may include the ease of attachment of a reagent, for example a polypeptide or a nucleic acid, to the material, which may be done prior to the said treatment of the bibulous material.

Nitrocellulose may be useful as the support material, as well known to those skilled in the art. Nitrocellulose is able to bind proteins without prior sensitisation. Immunoglobulin molecules, for example, may be immobilised on nitrocellulose without the need for a chemical treatment which might interfere with the specific binding activity of the immunoglobulin. Unused binding sites may be blocked as described above or using a material such as polyvinylalcohol (PVA). Nitrocellulose is available in a range of pore sizes; pore size may be selected to give the required sample flow rate. The nitrocellulose may preferably have a pore size of at least 1 μm. More preferably, the pore size is less than about 20 μm.

It will be appreciated that analyte molecules that become immobilised on the device as a result of interaction with the specific binding partner may thereafter not flow through the device at the same rate as other components, but it is preferred that before said immobilisation that the analyte molecules flow through the device at the same rate as other components.

The advantages of using a non-bibulous support may include that the speed of liquid flow along the support may be greater using a non-bibulous than a bibulous support. This may result in sample or reagent liquids reaching all portions of the detection or binding zone within a shorter period of time, which may be substantially the same for each said sample or reagent liquid, thus improving the consistency of timing of incubation across the detection and/or binding zone.

The sample receiving zone is capable of having the said liquid sample applied to it such that the liquid is able to flow into the lateral flow zone, which may comprise a detection and/or binding zone. Thus, the sample receiving zone may be a chamber in lateral flow contact with the lateral flow zone, which may comprise a detection and/or binding zone (ie lateral flow is possible between the lateral flow zone and the chamber). The chamber has an aperture through which the liquid sample is introduced into the chamber.

It is preferred that the sample receiving zone comprises a chamber, preferably with a volume between about 5 and 2000 μl, more preferably between about 10 and 200 μl.

Alternatively, the sample receiving zone may comprise a solid support capable of conducting lateral flow of the liquid sample into the detection or binding zone. The solid support preferably has good wettability and wicking action, as known to those skilled in the art and as described in U.S. Pat. No. 5,770,460, and low analyte and reagent retention properties. These properties may assist in the transfer of the liquid sample and the analyte or reagent to the detection or binding zone. It is preferred that the sample receiving zone, for example comprising a solid support, is capable of conducting non-bibulous lateral flow, as defined above.

The sample receiving zone may comprise a mechanical filter to remove particulate matter from the liquid sample. For example, the filter may be capable of removing cells from a sample, for example erythrocytes from a to blood sample, and/or of removing debris from a food or environmental sample, for example from a drinking water sample.

It will be appreciated that the sample receiving zone and a detection and/or binding zone may be in lateral flow contact via a zone (which may be part of the lateral flow zone) of the device, in which a reagent is present, for example a label reagent, as discussed further below.

The detection and/or binding zone comprises a capture reagent which is immobilised in the said detection and/or binding zone. The capture agent immobilised in a detection zone is such that the amount of a detectable label that remains in the detection zone when the assay is performed is a function of the presence/absence and/or concentration of the analyte in the liquid sample. By "immobilised" is meant that the capture reagent is retained in the said detection zone throughout the assay procedure.

Suitable combinations of capture reagent, analyte and detectable label will be well known to those skilled in the art. However, it will be appreciated that the device of the invention is suitable for performing assays in which washing steps and/or incubations of predefined and precise duration are required. Known assay devices may not be suitable for the performance of assays of these types; thus the range of assays that may be performed using the device of the present invention may be greater than the range possible with known devices, such as those described in U.S. Pat. No. 5,770,460.

The capture reagent may be a biological molecule, for example a polypeptide, nucleic acid, lipid or polysaccharide. Methods of attaching such a capture reagent to a solid support or surface are well known to those skilled in the art and are discussed further below. Such means may include covalent attachment, adsorption or physical entrapment methods. Methods involving in situ synthesis, as well known to those skilled in the art, may be employed. Adsorbtion may be achieved by drying of a solution or suspension of the capture reagent on the device, for example on a solid support member or on a wall of the capillary chamber. Derivatization, for example of a membrane (solid support) may permit covalent bonding, for example using glutaraldehyde or a carbodiimide. The capture reagent may be attached to another material which may be physically entrapped in the detection and/or binding zone or otherwise immobilised in the detection and/or binding zone by any physical, chemical or biological means. Thus, the capture reagent may be present on beads which may be trapped in the solid support in the detection and/or binding zone.

The first and second portions and/or the substantially planar plate may cooperate to form a chamber for receiving the absorbent pad. The chamber may enclose the absorbent pad such that the absorbent pad is not in liquid communication with the exterior of the device (other than any communication through the lateral flow zone), so that liquid held in the absorbent pad is substantially unable to leak out of the device. It is preferred that the chamber encloses the absorbent pad as described above when the second portion is in the second position relative to the first portion ie when the absorbent pad is in intimate contact with the lateral flow zone.

It will further be appreciated that the present device may be suitable for use in an automated procedure. Thus, addition of liquids to the sample receiving zone and movement of the second portion of the device between the said two positions relative to the first portion may be undertaken by a robotic system.

The device may be disposable. It may be sterilisable, for example by autoclaving or irradiation, as well known to those skilled in the art. Preferably, the device is formed such that disassembly of the device is not required for determination of the assay result.

The first and second portions may be configured and arranged such that the second portion is locked or is lockable in relation to the first portion once it has been moved to the second position ie the device becomes locked or is lockable in a conformation in which the absorbent pad is held in intimate contact with the lateral flow zone. Suitable cooperating means on the first and second portions will be known to those skilled in the art. In one alternative arrangement, the device may comprise spring means which serve to return the second portion to the first position once a force required to move the second portion to the second position has been removed.

It will be appreciated that a further aspect of the invention provides a portion or moulding for forming part of an assay device, the portion being configured to be permanently or removably attachable to a substantially planar plate such that a part of said portion forms a capillary chamber between said plate and the said portion and a part of the said portion participates in forming a sample receiving zone, wherein the said sample receiving zone and said capillary chamber are in contact (ie in lateral flow contact). Preferably, a part of the portion participates in forming a chamber capable of accommodating an absorbent pad, wherein the chamber is in contact with the capillary chamber. Preferably, the sample receiving zone and the chamber are in lateral flow contact via the capillary chamber.

It is preferred that the first portion and/or second portion is or comprises a plastics moulding. It will be appreciated that the moulding may be formed by processes including moulding and/or other shaping or finishing procedures, for example pressing, as are well known to those skilled in the art. It will be appreciated that the methods employed in providing the moulding are not critical to the performance of the invention.

The moulding may, for example, comprise or be formed of any suitable plastic, as known to those skilled in the art. It is preferred that the plastic is a hydrophilic plastic. Preferred plastics may include polymethymethacrylate (PMMA), polyvinylchloride, polycarbonate or polystyrene, for example styrene-acrylonitrile polymer (SAN). Polypropylene and polyethylene are less preferred. Polycarbonate is particularly preferred. It will be appreciated that in some applications, for example those requiring densitometric measurements, it may be desirable for the plastic to be a clear or colourless plastic. If detection is by means of fluorescence, it may be desirable for the plastic to be coloured, preferably darkly coloured, for example black. It may be desirable that the portion or comprises material, for example copper, with high thermal conductivity, as discussed below.

The first and/or second portion may be permanently or removably fixed to the substantially planar plate. Thus, for example, the first portion/moulding may be bonded, for example using an adhesive, or clipped onto the plate. Suitable adhesives will be well known to those skilled in the art. Preferably the portion/moulding is clipped onto the plate.

The absorbent pad may comprise any porous or fibrous material capable of absorbing liquid rapidly, as described, for example, in U.S. Pat. No. 5,656,503. The porosity of the material can be unidirectional (ie with pores or fibres running wholly or predominantly parallel to an axis of the member) or multidirectional (omnidirectional, so that the zone or pad has an amorphous sponge-like texture). A porous plastic material such as polypropylene, polyethylene (preferably of very high molecular weight), polyvinylidene flouride, ethylene vinylacetate, acrylonitrile and polytetrafluoroethylene can be used. Paper or other cellulosic materials such as nitrocellulose may also be used. A glass or other fibre filter may be used. Material similar to that used in the tips of fibre tipped pens may be suitable. It may be desirable to treat the material with a surface-active agent to reduce any inherent hydrophobicity. It is preferred that the material is robust both when dry and when moist such that the material retains its shape and can therefore accurately be moved from a position in which it is not in contact with the detection or binding zone to a position in which it is in such contact. Examples of suitable absorbent materials include ED No 939 absorbent and Whatman 3 MM chromatography paper. A preferred absorbent material is CD427, supplied by Whatman International Ltd, Whatman House, St Leonards Road, 20-20 Maidstone Allington, Maidstone ME16 0LS.

It will be appreciated that the properties of the absorbent zone or pad may determine how rapidly liquid is drawn through the capillary chamber from the sample zone or chamber to the absorbent zone or pad. Methods of assessing the properties of the absorbent material will be well known to those skilled in the art. Details of the properties of the absorbent material may routinely be provided with the absorbent material by the supplier.

It is preferred that the porous pad is capable of absorbing a volume of liquid at least equal to the volume of test sample and any reagents, including washing reagents, used during the assay. It will be appreciated that it may be desirable to perform three washing steps in between addition of reagents. It will be appreciated that the absorbent pad may comprise one or more absorbent materials, which may have different absorbent properties, as known to those skilled in the art. The pad may be capable of absorbing a volume of liquid of between about 5 and 50 times the volume of the capillary chamber, for example about 30 times or 10 times the volume of the capillary chamber.

A still further aspect of the invention provides a kit of parts comprising a portion for forming part of an assay device as described above and a substantially planar plate to which the portion is capable of being permanently or removably attached as said. The said substantially planar plate may have immobilised on it a capture reagent or reagents as discussed above. Thus, the said substantially planar plate may have immobilised on it an array of capture reagents. Alternatively or in addition to the substantially planar plate, the kit may comprise a second portion which holds or is arranged to hold an absorbent pad. Preferably, the second portion is capable of holding the said absorbent pad in the chamber capable of accommodating an absorbent pad. The kit may further comprise a spacer, as discussed further below. The kit may further comprise an absorbent pad which can be held by the second portion. The kit may still further comprise reagents suitable for carrying out an assay in relation to one or more of the capture reagent(s) immobilised on the substantially planar plate.

A further aspect of the invention provides a method of forming an assay device of the invention comprising the step of permanently or removably attaching a substantially planar plate as defined in relation to the kit of parts to a portion for forming part of an assay device as described above.

The method may further comprise the step of attaching a second portion which holds or is arranged to hold an absorbent pad to the substantially planar plate and/or the portion for forming part of an assay device. It will be appreciated that the first and second portion and the substantially planar plate may be assembled in any appropriate order.

A further aspect of the invention provides the use of a substantially planar plate as defined above and/or a portion for forming part of an assay device as defined above and/or a second portion which holds or is arranged to hold an absorbent pad, in forming an assay device according to the invention.

A further aspect of the invention provides the use of an assay device of the invention in a method of quantifying or detecting the presence or absence of an analyte in a liquid sample, wherein the liquid sample is applied to the said device. A further aspect of the invention provides a method of quantifying or detecting the presence or absence of an analyte in a liquid sample, comprising the steps of applying the liquid sample to a device of the invention. Preferably, the device of the invention is in the first position when the liquid sample is applied to the device, and the method further comprises the step of moving the second portion to the second position. The step of moving the second portion may be performed after a desired time has elapsed since the application of the liquid sample to the device. Thus, the device may be used in a method of performing a timed incubation ie in performing an assay method that requires a timed incubation. Further details of such methods or uses are given below.

It will be appreciated that the device may be useful in determining whether a specific binding partner, for a reagent present in the liquid sample, is present in a test sample immobilised on the device, preferably in the lateral flow zone. Thus, the device may be useful, for example, in performing an in situ hybridisation assay, a term well known to those skilled in the art. Thus, the test sample, for example cells or a tissue sample, may be immobilised on the device in the lateral flow zone. Liquid reagent(s) to be applied to the test sample may be supplied to the sample receiving zone. Such a reagent may comprise a probe reagent, for example a labelled nucleic acid, antibody or antibody fragment, which is capable of binding specifically to the said specific binding partner that it is desired to detect. Further reagents may include washing/rinsing reagents and reagents necessary to detect the probe reagent, as well known to those skilled in the art.

It will be appreciated that a device according to the invention may also be useful in performing other incubations in which a specific binding interaction is not necessarily required. Thus, the said device may be useful in incubating cells that are immobilised on the device, for example in the lateral flow zone, with successive different media or non-specific staining reagents. The different media may comprise, for example, different concentrations or types of biologically active compounds; for example, the device may be useful in exposing cells to a growth factor.

It will be appreciated that some embodiments of the above device may not be suitable or preferred for performing incubations of cells. Thus, embodiments in which the lateral flow in the lateral flow zone occurs through a solid support, for example through the length of a membrane, may not be preferred for such incubations. Embodiments in which the lateral flow in the lateral flow zone occurs through a capillary chamber may be particularly preferred for performing such incubations.

The device may be particularly suitable for use in the performance of assays in which the result is detected using a microscope or other instrument and/or automated assays. The device may also be suitable for carrying out multiple assays on a sample in a single device. The device is further useful in performing other timed incubations, particularly when it is desired to minimise the quantity of reagents used.

BRIEF DESCRIPTION OF THE DRAWINGS

The invention will now be described, by way of example only, with reference to the drawings, of which:

FIG. 2 shows an exploded perspective view of components of a device prior to assembly.

FIG. 3 shows a perspective view of an assembled device.

FIG. 4 shows a view of a first portion of a device.

FIG. 5 shows views of a device with the second portion in the first and second positions.

FIG. 6 shows elevations of an assembled device.

DETAILED DESCRIPTION

As shown in FIGS. 2 to 7, the invention provides a device generally comprising a first moulding 1, a substantially planar plate 2, an aperture 6 leading to the sample receiving chamber 7, a spacer 4, capillary chamber 3, absorbent pad 8, immobilised capture reagent 9, second moulding 10 and locking means 11.

The first portion or moulding 1 is permanently or removably attached to a substantially planar plate such as a glass or polycarbonate slide 2 such that a part of said moulding 1 forms a capillary chamber 3 between said plate 2 and the said moulding, the device further comprising a chamber 5 into which a test sample and/or reagent can be introduced and further comprising a chamber 7 capable of accommodating an absorbent pad 8, wherein the said chamber into which a test sample and said chamber capable of holding an absorbent pad 8 are in lateral flow contact via the said capillary chamber 3.

The device further comprises a second portion or moulding 10 to which is attached an absorbent pad 8, wherein the said absorbent pad 8 is held by the said second moulding 10 in the said chamber 7 capable of accommodating an absorbent pad.

Figure 5:
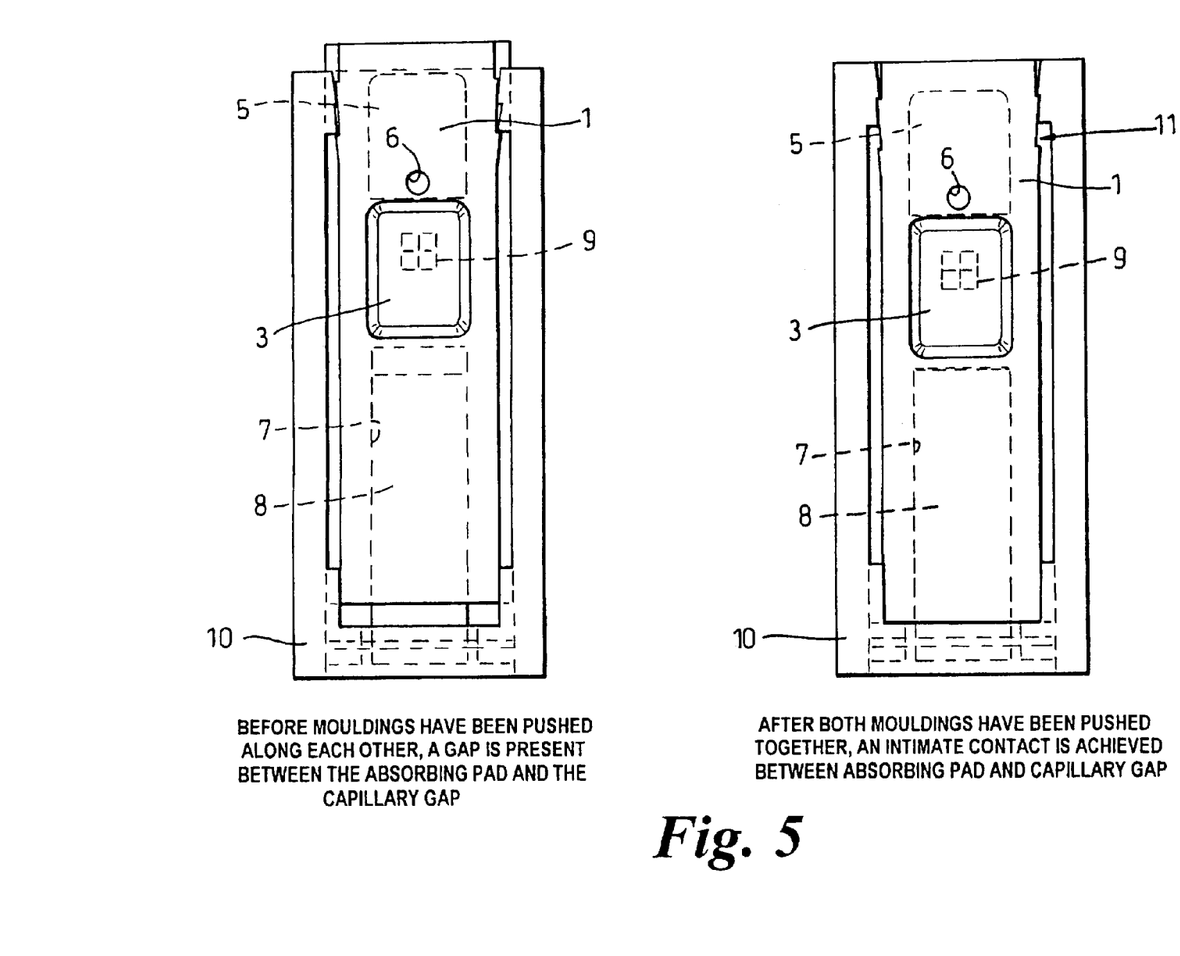
Figure 6:
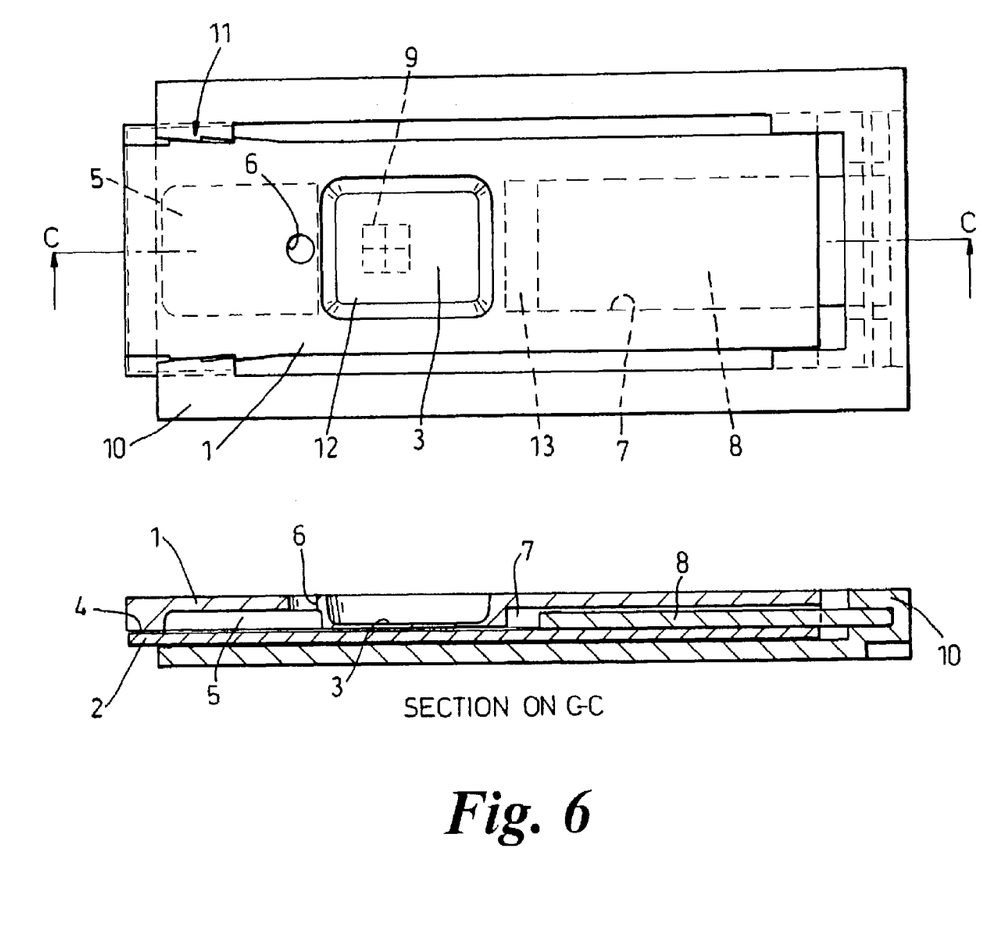

The device has at least two conformations, characterised in that in a first said conformation the absorbent pad 8 is not in lateral flow contact with the said capillary chamber 3 and wherein in a second said conformation the absorbent pad 8 is in lateral flow contact ie is in intimate contact with the said capillary chamber 3.

The transition between the two conformations may be effected by moving the second moulding 10 in relation to the first moulding 1 and/or said planar plate 2. Preferably, the second moulding 10 is capable of sliding along the first moulding and/or said planar plate 2.

The planar plate 2 preferably has dimensions substantially those of a standard laboratory microscope slide (see, for example, Sigma microscope slides; product numbers S8902, S8400 or S9027: Sigma-Aldrich Company Ltd, Fancy Road, Poole, Dorset, BH12 4QH, UK). The dimensions of a standard laboratory microscope slide are about 25 mm×75 mm×1 mm. It is preferred that the said planar plate is such a standard glass or plastic microscope slide. Such a plate may have the advantage of being readily available, of a size to fit in standard laboratory equipment, and of appropriate surface properties to support capillary flow and to allow attachment of biological molecules, for example polypeptides or nucleic acids, to its surface, as known to those skilled in the art. Glass is preferred for its optical properties and because of the ease with which molecules such as nucleic acids and polypeptides may be attached to a glass surface. However, it will be appreciated that an optical grade plastic, for example optical grade polycarbonate may be used in place of glass.

The chamber 5 into which the test liquid may be introduced may have an aperture 6 through which the test liquid is introduced into the chamber. Reagents may further be introduced into the chamber 5 at the same time as, or before or after, the test liquid. Once the test liquid and/or reagent(s) has been drawn into the capillary chamber and optionally through the chamber into the absorbent pad, a further liquid sample and/or reagent may be added to the chamber 5. Thus, for example, a washing reagent, for example distilled water or a suitable buffer solution, may be added. The liquid may be introduced via the aperture by means of manual administration of the liquid, for example using a pipette or syringe, or by automated administration, for example by a robot-type machine. The volume of the chamber 5 is preferably between about 5 and 2000 or 4000 μl. Preferably, the volume of the chamber 5 is between about 10 or 20 and 500 or 1000 μl, still more preferably between about 10 or and 200 or 400 μl.

It will be appreciated that the device may comprise a sample-receiving chamber 5 and a further chamber (not shown) to which a further sample or reagent may be added. Thus, the device may comprise a chamber of volume less than, for example, 50 μl into which the test sample may be introduced, and a chamber of a volume between, for example, 200 μl and 1500 μl to which a reagent, for example a washing reagent, may be introduced.

The second portion or moulding 10 may similarly be formed of a plastics material. The second moulding 10 may fit onto the said first moulding 1, for example when bonded to the said planar plate 2, and may be capable of sliding along the first moulding 1 from a first position to a second position. The absorbing pad 8 is held by the second moulding 10, for example by means of a push fit or through bonding, for example using an adhesive. In a first position of the second moulding 10 relative to the first moulding 1 and/or plate 2, there is a gap between an open edge of the capillary chamber 3 and the absorbent pad 8, such that liquid present in the capillary chamber 3 is not in contact with the absorbent pad 8 and is not drawn into the absorbent pad 8. In a second position of the second moulding 10, the absorbent pad is in contact, preferably close or intimate contact, with the open edge of the capillary chamber 3, such that liquid present in the capillary chamber 3 is in contact with the absorbent pad 8 and is drawn out of the capillary chamber 3 into the absorbent pad 8. It will be appreciated that as liquid is drawn out of the capillary chamber 3 into the absorbent pad 8, any further liquid present in the sample chamber 5 (or additional chamber as discussed above) may be drawn into the capillary chamber 3 and further into the absorbent pad 8.

It will be appreciated that the said second moulding 10 may be moved between said first and second positions, for example from said first position to said second position and then back to the said first position, repeatedly such that liquid may be drawn into and out of the capillary chamber 3 under the control of the operator (which may be a robotic system). Thus, the time for which a given liquid remains in the capillary chamber 3 may be controlled by the operator. The device may be sprung, such that the device reverts to one of said first and second positions unless continuous force is applied to the device. Alternatively, the device may be formed such that once the said second moulding 10 has been moved to said second position, it is locked in that position. Locking means 11 are indicated, for example, in FIGS. 4, 5 and 6 and may comprise cooperating structures, as well known to those skilled in the art, on the first and second portions such that movement from the first position to the second position is permitted whilst movement from the second to the first position is resisted.

The said second moulding 10 may interact with the said first moulding 1 in such a manner that the two mouldings are not easily accidentally disassembled. This may be desirable in preventing contents of the device, in use, from being spilt. Preferably, the device does not have to be disassembled in or following use.

As indicated above, the speed with which liquid enters and is drawn out of the chamber 5 may vary depending upon the properties of the liquid, capillary chamber 3 and absorbent pad 8. However, it will be appreciated that these times may be short in comparison to the periods for which it may be desirable for a liquid to remain in the capillary chamber 3.

The device may be useful in the performance of assays as described below. Antigen may be used, for example as the capture reagent, in the detection of antibody (the analyte) capable of binding to the antigen, and vice versa. A variety of immunoassay techniques will be known to those skilled in the art in which the final read-out of the assay reaction involves a reagent conjugated with an appropriate detectable label. Radiolabelling, for example with $^{131}$I, $^{125}$I, may be used. However, a label which may be detected by visual or fluorescent means may be preferred. Thus, the specific recognition when detecting an antigen is provided by the primary antibody (polyclonal or monoclonal) but the secondary detection system can utilise fluorescent, enzyme, or other conjugated secondary antibodies.

The binding of labelled antigen (for example radioactively or fluorescently labelled) to a fixed amount of antibody (the capture reagent: immobilised in the detection and/or binding zone) can be partially inhibited by addition of unlabelled antigen (the analyte being tested for in the liquid sample), and the extent of this inhibition can be used as a measure of the unlabelled analyte added.

The content of antibody specific for a particular antigen in, for example, a serum can be assessed by the ability to bind to antigen which is immobilised in the detection zone (the capture reagent); the bound immunoglobin may then be estimated by addition of a labelled anti-Ig raised for another species. It will be appreciated that such an assay requires a washing step to remove unbound immunoglobulin from the detection zone. Thus, this type of assay cannot readily be performed using test devices in which washing is not envisaged but may readily be performed using a device of the invention. For example, a patient's serum (liquid sample) is added to the sample receiving zone 5 and flows into the detection zone 9 (in the lateral flow zone ie capillary chamber 3) in which immobilised antigen (capture reagent) is present. Antibodies of the appropriate specificity bind to the immobilised antigen. The liquid sample is drawn out of the detection zone 9 in the capillary chamber 3 by bringing the absorbent zone 8 into lateral flow contact with the capillary chamber 3 (ie placing the device into the said second conformation). Wash buffer is then added to the sample receiving zone 5 and remaining serum proteins are washed from the capillary chamber 3 (incorporating the detection zone 9) into the absorbent zone 8 as the wash buffer flows through the lateral flow zone and hence detection zone. Bound antibody can then be estimated by addition of a solution of labelled anti-immunoglobulin, for example anti IgG, anti IgM, anti IgA or anti IgE, antibody or antibody fragment to the sample receiving zone 5, followed by further wash buffer. The labelled anti-immunoglobulin antibody or antibody fragment may, for example, be $^{125}$I-labelled or fluorescently-labelled purified rabbit anti IgG. This may be detected by methods known to those skilled in the art, for example using a fluorescence imaging device.

Figure 1:
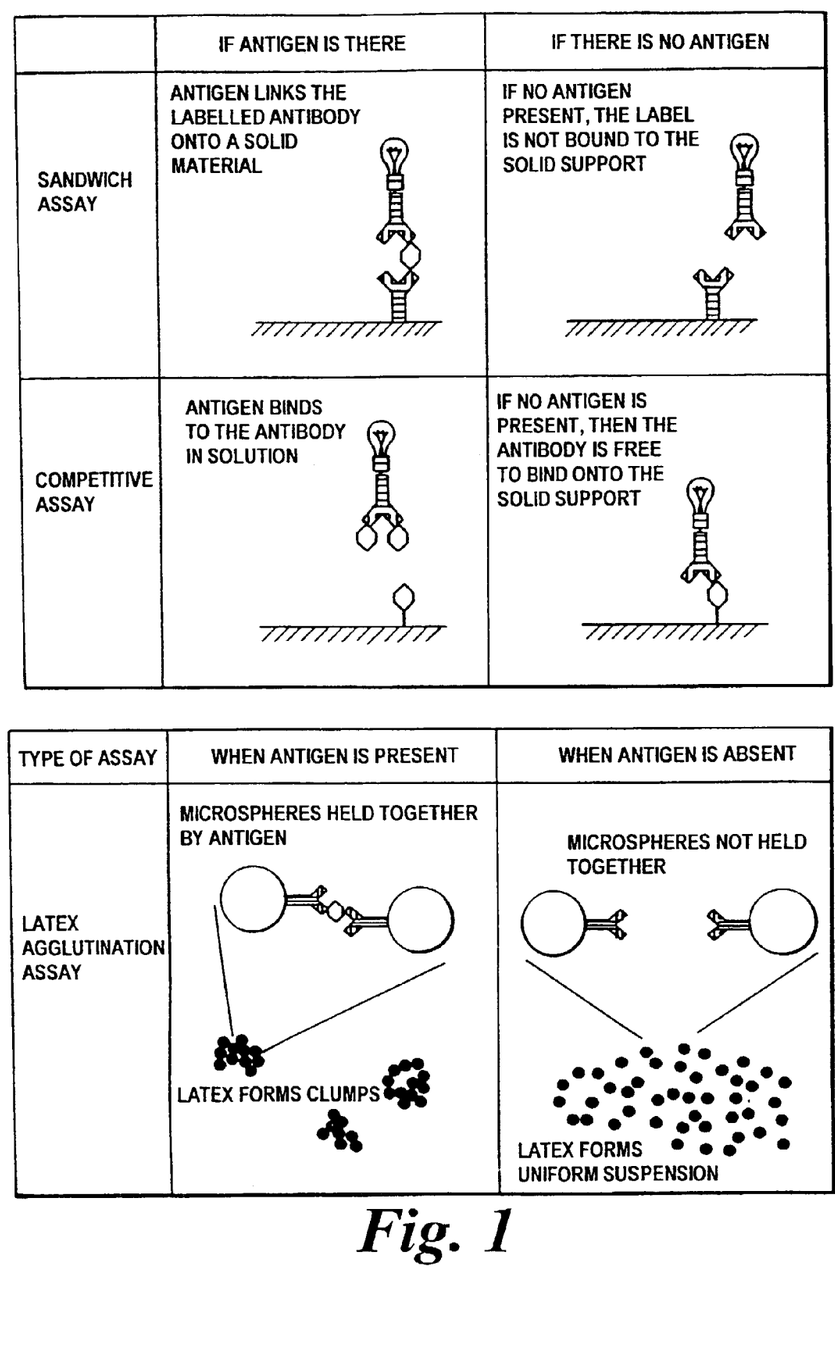
FIG. 1 shows examples of suitable assay principles that may be used in a device of the invention, including a solid phase immunoassay for antibody. By attaching antibody to the solid phase, the system can be used to assign antigen. To reduce non-specific binding of IgG to the solid phase after absorption of the first reagent, it is usual to add an irrelevant protein such as gelatin, or more recently $\alpha_1$-glycoprotein, to block any free sites on the support.
Figure 2:
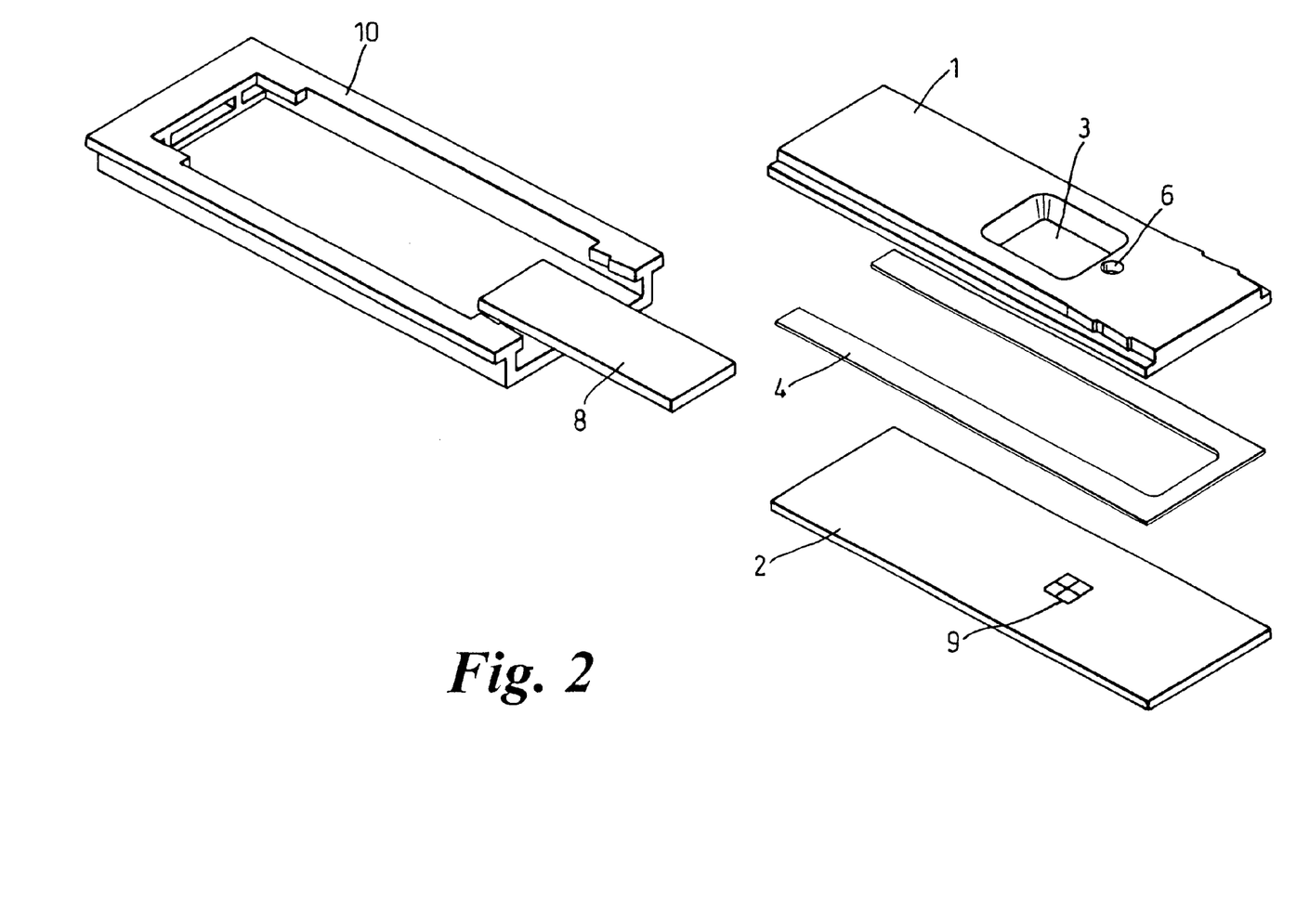
FIGS. 2 to 6 show views of a device of an embodiment of the invention.
Figure 3:
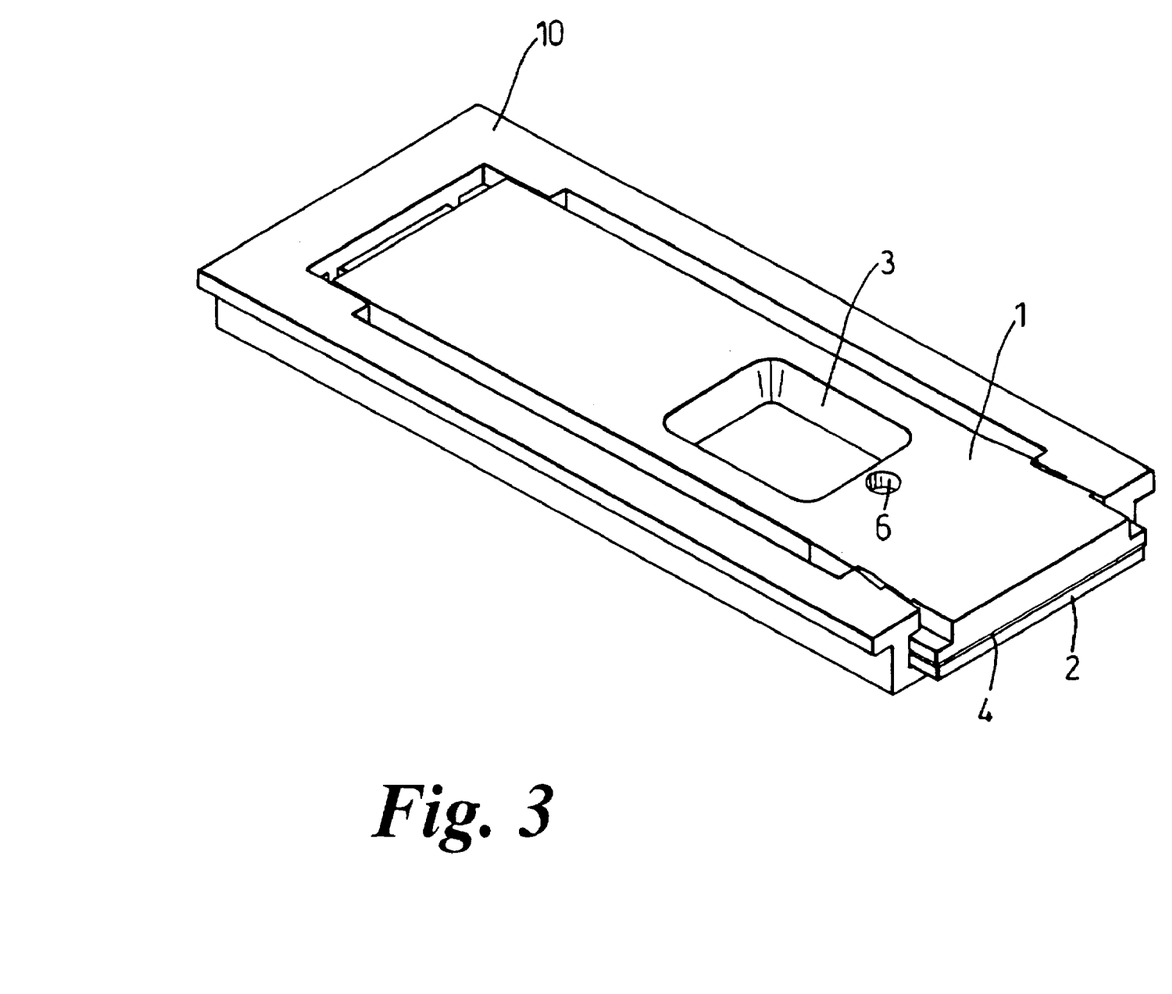
Figure 4:
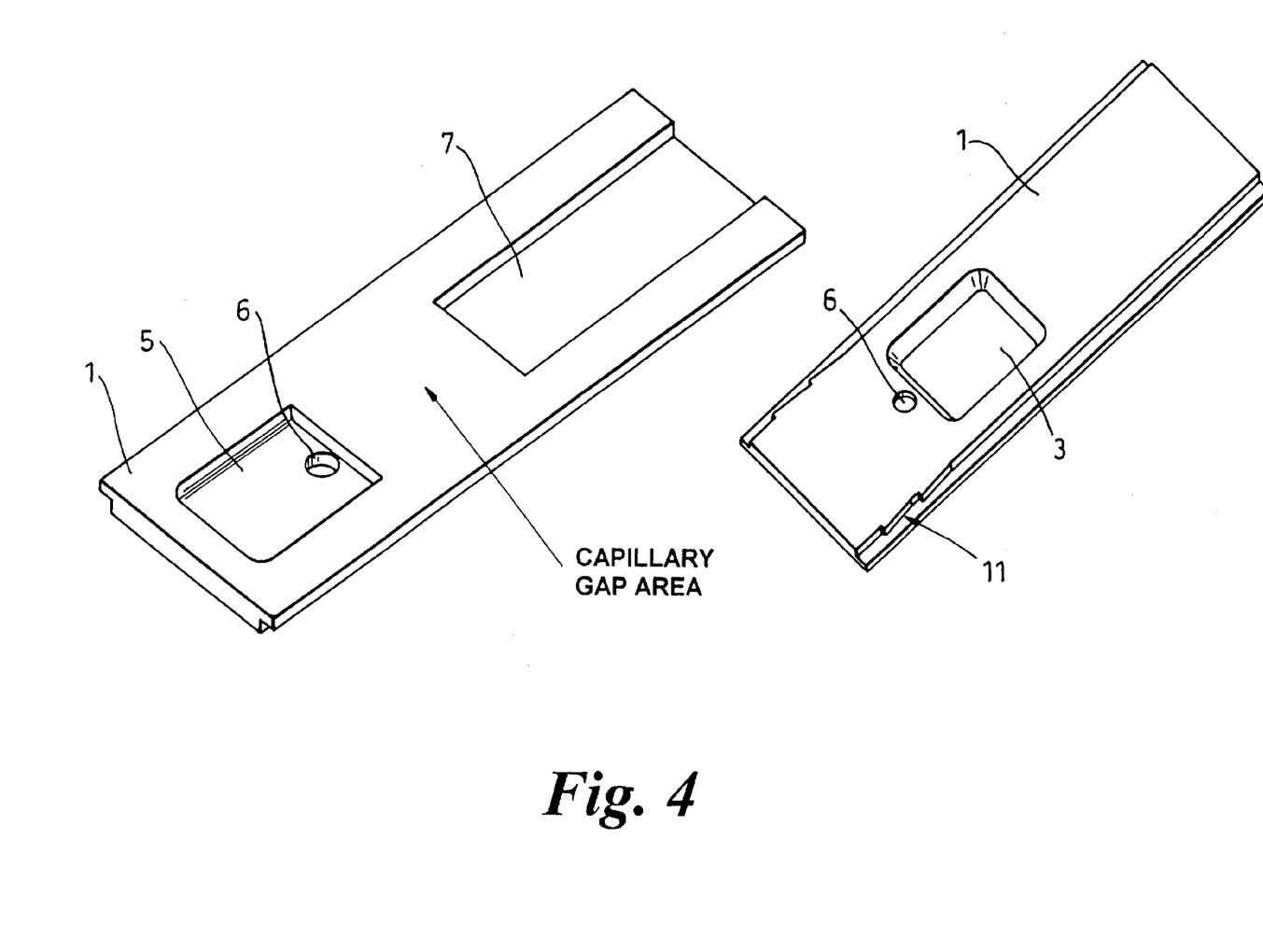

For the estimation of antigen, for example, antibodies (capture reagent) are immobilised in the detection zone 9 and the liquid test sample which is being tested for the antigen (analyte) is added to the sample receiving zone 5 and drawn into the detection zone 9. The device is placed into the said second conformation, such that the liquid test sample is drawn out of the detection zone 9 into the absorbent zone 8. After washing, as described above, the amount of antigen bound in the detection zone 9 can be estimated by adding an excess of labelled antibody, for example fluorescently labelled antibody. The specificity of the method can be improved by the sandwich assay method, as shown in FIG. 1 and FIG. 2, in which the immobilised antibody and labelled antibodies have specificities for different parts of the antigen.

It will be appreciated that an assay system similar to those described in U.S. Pat. No. 5,770,460, for example, may be used. In one such system, the liquid sample is brought into contact with a labelled reagent which binds the analyte specifically. The capture reagent immobilised in the detection zone 9 binds specifically to a different site on the analyte from the labelled reagent, such that the labelled reagent and the capture reagent may simultaneously bind to a molecule of the analyte. The labelled reagent may be added to the liquid sample in the sample receiving zone 5 or it may be present in a labelling zone 12 between the sample receiving zone 5 and the detection zone 9, as mentioned above. The labelling zone 12 may be in the lateral flow zone ie in the capillary chamber 3. As the liquid test sample passes through the labelling zone 12, the labelled reagent binds to the analyte in the test sample. The liquid flow carries the labelled reagent into the detection zone 9. Labelled reagent that is bound to analyte is retained in the detection zone 9 by binding of the analyte to the capture reagent. Labelled reagent that is not bound to analyte is not retained in the detection zone 9.

In a second such approach, the labelled reagent competes with the analyte for binding to the capture reagent in the detection zone 9. Thus the presence of analyte in the liquid test sample leads to a lower level of labelled reagent retained in the detection zone 9 than in the absence of analyte in the liquid test sample.

It will be appreciated that it is preferred that any two of the capture reagent, analyte, label reagent or other reagent required by the assay design, as appropriate depending on the assay design, interact specifically. At least one of the capture reagent, label reagent or other reagent required by the assay design interact specifically with the analyte ie is a specific binding partner for said analyte. It is preferred that the interaction if of high affinity. By "high affinity" is meant an interaction with a $K_d$ of between $10^{-8}$ and $10^{-16}$ M, preferably between $10^{-13}$ and $10^{-16}$ M. By "interact specifically" is meant that the said components interact with at least 100-fold higher affinity (and preferably at least 500-fold, or at least 1000-fold, or at least 2000-fold higher affinity) with the intended binding component than with other molecules that may be encountered by either of the said components when performing the assay, for example on a sample taken from a patient, for example blood, serum or urine, or on a food/drink or environmental sample.

Enzymes which give a coloured reaction product may be used as the labelled reagent. Enzymes such as horse radish peroxidase and phosphatase have been widely employed in enzyme-linked assays. A way of amplifying the phosphatase reaction is to use NADP as a substrate to generate NAD which now acts as a coenzyme for a second enzyme system. Pyrophosphatase from *E. coli* provides a good conjugate because the enzyme is not present in tissues, is stable and gives a good reaction colour. Chemi-luminescent systems based on enzymes such as luciferase can also be used. Other suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur $^{35}$S), tritium ($^{3}$H), indium ($^{112}$In), and technetium ($^{99}$Tc), and fluorescent labels. Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a green fluorescent protein (GFP) fluorophore label and a fluorescamine label. Examples of chemiluminescent labels include a luminal label, an isoluminal label, an aromatic acridinium ester label, an imidazole label, an acridinium salt label, an oxalate ester label, a luciferin label, a luciferase label, and an aequorin label. Other suitable labels include nanoparticle probes and associated signal amplification methods based on nanoparticle-promoted reduction of silver, for example as described in Taton et al (2000) *Science* 289, 1757-1760 and references therein.

Typical techniques for binding the above-described labels to antibodies are provided by Kennedy et al., Clin. Chim. Acta 70:1-31 (1976), and Schurs et al, Clin. Chim. Acta 81:1-40

(1977). Coupling techniques mentioned in the latter are the glutaraldehyde method, the periodate method, the dimaleintide method, the m-maleimidobenzyl-N-hydroxy-succinimide ester method, all of which methods are incorporated by reference herein.

As an alternative to the enzyme, for example, being bound directly to a labelled reagent which binds to the analyte, the labelled reagent may be labelled with the vitamin biotin, as well known to those skilled in the art. The biotinylated reagent may then be readily detected by its reaction with enzyme-linked avidin or streptavidin to which it binds with great specificity and affinity, as well known to those skilled in the art.

As used herein, the term "antibody" (Ab) is meant to include intact molecules as well as antibody fragments (such as, for example, Fab and F(ab')2 fragments, synthetic antibody-like molecules such as single-chain Fv fragments (ScFv) and domain antibodies (dAbs), and other molecules with antibody-like antigen binding motifs) which are capable of specifically binding to, for example, the analyte. Fab and F(ab')2 fragments lack the Fc fragment of intact antibody. The suitability or otherwise of antibody fragments for use in particular assay protocols will be well known to those skilled in the art. It will be appreciated that it may be desirable to use a monoclonal antibody (Mab) or fragment in particular assay steps, as known to those skilled in the art. A general review of the techniques involved in the synthesis of antibody fragments which retain their specific binding sites is to be found in Winter & Milstein (1991) *Nature* 349, 293-299.

It will be appreciated that the analyte and an assay reagent, for example the capture reagent, may be nucleic acids, for example RNA or DNA. When analysing hybridisation of an analyte nucleic acid to an assay reagent, it may be important to control the temperature at which the assay is performed; in particular it may be necessary to perform different steps of the assay at different temperatures. Thus, it may be desirable that the device or a part thereof is constructed such that the device has good thermal conductivity from at least one exterior surface of the device to the detection or binding zone. Thus, a portion of the device in contact with or forming part of the detection or binding zone 9 may be formed from a material with good thermal conductivity, for example a metal, particularly copper, as well known to those skilled in the art. Thus, in an embodiment it is preferred that the temperature in the detection or binding zone 9 changes from at least 90° C. to less than 65° C. when in contact with a copper plate whose temperature changes from 96° C. to 60° C. over a period of 2 minutes, 1 minute or 30 s, in not more than a further 2 minutes, 1 minute, 30 s or 15 s after the said copper plate has reached 60° C.

Thus, it will be appreciated that a device of the invention may be used in an assay to detect the presence or absence or to quantify the amount present in a sample of an (analyte) nucleic acid that is capable of hybridising selectively to a second (reagent) nucleic acid. The reagent nucleic acid may be a capture reagent immobilised in the detection zone 9.

By "selectively hybridising" is meant that the analyte nucleic acid has sufficient nucleotide sequence similarity with the said second nucleic acid that it can hybridise under moderately or highly stringent conditions, and preferably does not hybridise to other similar nucleic acids under the same conditions. As is well known in the art, the stringency of nucleic acid hybridization depends on factors such as length of nucleic acid over which hybridisation occurs, degree of identity of the hybridising sequences and on factors such as temperature, ionic strength and CG or AT content of the sequence.

Typical moderately or highly stringent hybridisation conditions which lead to selective hybridisation are known in the art, for example those described in *Molecular Cloning, a laboratory manual,* 2nd edition, Sambrook et al (eds), Cold Spring Harbor Laboratory Press, Cold Spring Harbor, N.Y., USA, incorporated herein by reference.

It will be appreciated that nucleic acid amplification methods, for example polymerase chain reaction methods (PCR), QB replicase and ligase chain reaction methods, may be performed in a device of the invention or may be used in preparation of a sample for assay using a device of the invention. Also, NASBA (nucleic acid sequence based amplification), also called 3SR, can be used as described in Compton (1991) *Nature* 350, 91-92 and *AIDS* (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

A nucleic acid comprising a detectable label may be useful in performing an assay in a device of the invention. By "detectable label" is included any convenient radioactive label such as $^{32}P$, $^{33}P$ or $^{35}S$ which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Fluorophorequencher pairs or fluorescence polarisation may also be useful, as known to those skilled in the art. A fluorochrome or fluorescent label is preferred. Nanoparticle probes and associated signal amplification methods based on nanoparticle-promoted reduction of silver, for example as described in Taton et al (2000) *Science* 289, 1757-1760 and references therein may also be particularly useful.

It will be appreciated that more than one species of capture reagent may be immobilised in the detection or binding zone 9. Thus, the device may be suitable for conducting assays in relation to more than one analyte in a liquid sample. Thus, the detection or binding zone 9 may have immobilised on it an array of different capture reagents.

Such an array may be similar to an array used in a biological chip assay, as known to those skilled in the art and as described below. New technology, called VLSIPS™, has enabled the production of extremely small chips that contain hundreds of thousands or more of different molecular probes, as described, for example, U.S. Pat. No. 5,874,219 issued 23 Feb. 1999 to Rava et al. These biological chips or arrays have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips or arrays are useful in a variety of screening techniques for obtaining information about either the probes or the target molecules. For example, a library of peptides can be used as probes to screen for drugs. The peptides can be exposed to a receptor, and those probes that bind to the receptor can be identified.

Arrays of nucleic acid probes can be used to extract sequence information from, for example, nucleic acid samples. The samples are exposed to the probes under conditions that allow hybridisation. The arrays are then scanned to determine to which probes the sample molecules have hybridised. Sequence information can be obtained by careful probe selection and using algorithms to compare patterns of hybridisation and non-hybridisation. This method is useful for sequencing nucleic acids, as well as sequence checking. For example, the method is useful in diagnostic screening for genetic diseases or for the presence and/or identity of a particular pathogen or a strain of pathogen. For example, DNA arrays can be used to examine a nucleic acid sample from the virus to determine what strain it belongs to.

It will be appreciated that such biological chips are generally not disposable, whereas the present device may be disposable. A device of the invention may preferably comprise between 1 and 5, 10, 15, 20, 50, 100, 150, 200, 500, 1000 or 2000 different capture reagents, for example in the form of an array. It may be preferred that a device comprises between about 50 and 500 different capture reagents, for example 200 different capture reagents.

The array may be formed using methods well known to those skilled in the art. Thus, various printing techniques may be suitable, for example techniques using microsyringes, pens using metered pumps, direct printing and ink-jet printing. Suitable methods may be described or reviewed in, for example, U.S. Pat. No. 5,856,101, U.S. Pat. No. 5,143,854, WO92/10092, WO99/40105, Service (2000) *Science* 289, 1673, MacBeath & Schreiber (2000) *Science* 289, 1760-1763, de Wildt et al (2000) *Nature Biotech* 18, 989-994, and Irving & Hudson (2000) *Nature Biotech* 18, 932-933. Suitable printing solutions are also described or reviewed in these documents, and will be well known to those skilled in the art. For example phosphate buffered saline (PBS) solutions may be used, for example 1×PBS, optionally comprising a non-ionic detergent, for example a polyoxyethylene glycol sorbitan ester, for example a Tween® detergent such as Tween 20, Tween 40, Tween 60 or Tween 80, as known to those skilled in the art. Inclusion of a stabiliser (or potential inhibitor of evaporation) such as polyvinylpyrrolidone (PVP), sucrose or glycerol may also be beneficial.

It will be appreciated that if the capture reagents are arranged in an array that the same label, for example the same fluorescent entity, may be used in relation to each capture reagent/analyte, as the identity of the analyte(s) present may be determined from the location in the array of the signal from the captured label. Alternatively, if in a less preferred embodiment, the capture reagents are not present at separate and defined locations in the detection or binding zone 9 (for example, the capture reagents are mixed before being immobilised in the detection or binding zone 9), then it is preferred that different labels are used in relation to each capture reagent/analyte, such that the signals in relation to each analyte may be distinguished.

It will be appreciated that the signal need not be generated and/or measured in relation to each capture reagent immobilised in the detection zone 9. Thus, for example, a device comprising more than one capture reagent may be sold (for example, with suitable additional reagents) as suitable for performing an assay in relation to any one (or more) of the capture reagents. No meaningful signal may be generated in relation to the capture reagents for which additional necessary reagents are not added during use of the device. Thus, one type of device may be sold for use in relation to several single or multiple-analyte assays.

It will be appreciated that it may be desirable to include on a device only capture reagents that are compatible, in that the same sequence of assay steps may be used in relation to each capture reagent/analyte assay. Thus, capture reagents that do not require a wash step in the associated assay may be grouped on an assay device. Capture reagents that do require a wash step in the associated assay may similarly be grouped together. This may have the advantage that results for every capture reagent/analyte assay, or any combination of different the capture reagent/analyte assays available, may be obtained, if desired, from a single test liquid sample. However, it will be appreciated that it is not essential that capture reagents are grouped in this way.

It is preferred that the results may be obtained using the same detection method in relation to each capture reagent included in a device. Thus, it is preferred that, for example, a fluorescent label is used in relation to each said capture reagent. Alternatively, a visually detectable label may be used in relation to each said capture reagent. It will be appreciated that a device in which more than one species of capture reagent is immobilised may be particularly suitable for use in an automated procedure and/or a procedure in which the assay results are not determined by unaided visual examination.

It will be appreciated that assays relating to each immobilised capture reagent in a device may be performed, particularly when using an automated system, but the results of selected assays only may be communicated to the user. Thus, reagents relating to all the capture reagents may be delivered to the device and the signal relating to each capture reagent may be determined, but only results for the assays for which the user has paid may be communicated to the user. Further results may be obtained on payment of additional fees, which may occur by means of an electronic credit system. Thus, if, for example, the device comprises capture reagents suitable for use with reagents for which detection apparatus is required, the user may be required to pay a fee per result reported, even if meaningful signals have been generated in relation to each capture reagent/analyte.

It will be appreciated that the physical or chemical properties of the device may determine which capture reagents may be incorporated into a device and therefore which combinations of capture reagent are possible in a given embodiment of the device.

It will be appreciated that the concentration or choice of additional reagents, for example labelled antibodies, relating to each capture reagent, may be such that the time required for each step of an assay may be satisfactory or optimal for each capture reagent for which it is desired to determine the presence or concentration of the relevant analyte. Thus, if a first analyte/labelled antibody pair has a higher affinity of binding than a second analyte/labelled antibody pair, then the concentration of the said second labelled antibody used in the assay may be higher than the concentration of the first said labelled antibody.

It is preferred in some circumstances that the binding of at least a portion of the analyte to a specific binding partner for said analyte is capable of being detected by means of a visual signal. Labels that may be used in providing a visual signal are well known to those skilled in the art, and include reagents such as gold sols or dye sols, coloured latex particles (for example of between about 0.05 and 0.5 microns), liposomes or cells, as described, for example, in U.S. Pat. No. 5,656,503, U.S. Pat. No. 4,943,522 and U.S. Pat. No. 5,770,460. A visual signal may be preferred if the device is to be used by a patient, or by a medical practitioner for obtaining an immediate result. It may be beneficial if the detection zone 9 has a background of contrasting colour to the visual signal to aid observation of the visual signal when viewed against the background. If the device comprises a solid support as described above, this may be of a contrasting colour in relation to the visual signal.

It may alternatively be preferred that the said binding of at least a portion of the analyte to a specific binding partner for said analyte is capable of being detected by means of a fluorescent or chemiluminescent signal. Fluorescent and chemiluminescent labels are described above. A fluorescent or chemiluminescent signal may be preferred if the device is to be used in an automated test procedure, particularly if it is desired to assay more than one analyte in a device.

The device may be useful in testing for analytes in samples such as blood, serum or urine or in environmental samples, for example drinking water, or food or drink samples.

Suitable analytes will be well known to those skilled in the art and include any molecule for which a specific binding partner is can be found, for example an antibody that is capable of binding specifically to the said molecule. Examples are given in U.S. Pat. No. 5,770,460, U.S. Pat. No. 4,943,522 and U.S. Pat. No. 5,656,503 (incorporated herein by reference) and include hormones, drugs, for example drugs of abuse, bacterial or viral antigens, immunoglobulins, cancer antigens, cytokines, allergens and nucleic acids.

The invention claimed is:

1. An assay device for quantification or detection of the presence or absence of an analyte in a liquid sample, comprising:
   (a) a first sub-assembly;
   (b) a capillary chamber;
   (c) a sample receiving zone in the first sub-assembly permanently fixed in relation to and in contact with the capillary chamber;
   (d) a second sub-assembly comprising a holder to accommodate an absorbent pad; and
   (e) wherein the first and second sub-assemblies are arranged in movable sliding relation relative to each other such that in a first position there is a gap between the holder of the second sub-assembly and the capillary chamber and in a second position the holder of the second sub-assembly is in contact with the capillary chamber, and wherein the capillary chamber is between said sample receiving zone and said holder.

2. A device as in claim 1 wherein the capillary chamber has a first edge in contact with the sample receiving zone and a second edge that contacts said holder of said second sub-assembly and wherein the depth of the capillary chamber is greater at the first edge of the capillary chamber in contact with the sample-receiving zone than at the second edge of the capillary chamber that comes into contact with said holder.

3. A device as in claim 2 wherein the device comprises a planar plate, wherein said planar plate or a portion thereof forms a wall of the capillary chamber.

4. A device as in claim 1 wherein the device comprises a planar plate, wherein said planar plate or a portion thereof forms a wall of the capillary chamber.

5. A device as in claim 1 wherein the capillary chamber comprises a zone selected from the group consisting of a detection zone and a binding zone or a combination thereof.

6. A device as in any one of claim 1, 2 or 4 wherein at least a portion of the planar plate or a portion of a wall of the capillary chamber is transparent to radiation selected from the group consisting of visible, UV aid/or infra-red radiation.

7. A device as in claim 4 wherein said planar plate is a microscope slide.

8. A device as in claim 7 wherein the said microscope slide is a glass microscope slide.

9. A device as in claim 1 wherein the first and/or second sub-assembly comprises a plastic molding.

10. A device as in claim 1 wherein the device comprises material with high thermal conductivity.

11. A device as in claim 10 wherein said material with high thermal conductivity comprises copper.

12. A device as in either of claim 10 or 11 wherein said capillary chamber is in contact with or comprises in part said material with high thermal conductivity.

13. A device as in claim 1 wherein the device is adapted to utilize a visual signal in quantification or detection of the presence or absence of an analyte in a liquid sample.

14. A device as in claim 1 wherein the device is adapted to utilize a fluorescent signal in quantification or detection of the presence or absence of an analyte in a liquid sample.

15. A method of forming an assay device comprising permanently or removably attaching a planar plate to an assembly such that a first sub-assembly of said assembly forms a planar capillary chamber between said plate and said assembly and participates in forming a sample receiving zone on one side of said capillary chamber, such that said sample receiving zone and said capillary chamber are in permanent fixed contact, the method further comprising slidingly attaching a second sub-assembly to the first sub-assembly, the second sub-assembly comprising a holder to accommodate an absorbent pad, whereby the holder of the second sub-assembly is moveable relative to the capillary chamber such that said holder can be moved in and out of contact with a second side of said capillary chamber.

16. A method as in claim 15 further comprising immobilizing one or more capture reagents on said planar plate.

17. A method as in claim 15 further comprising attaching the second sub-assembly to the planar plate and/or the first sub-assembly for forming part of an assay device.

18. A method of quantifying or detecting the presence or absence of an analyte in a liquid sample, comprising:
   (a) applying the liquid sample to a device comprising:
      1) a first sub-assembly;
      2) a capillary chamber;
      3) a sample receiving zone in the first sub-assembly in permanent contact with a first side of the capillary chamber;
      4) a second sub-assembly comprising a holder to accommodate an absorbent pad; and
      5) wherein the first and second sub-assemblies are arranged in sliding relation to each other such that in a first position there is a gap between the holder of the second sub-assembly and the capillary chamber and a second position in which the holder of the second sub-assembly is in contact with a second side of the capillary chamber;
   wherein the device is in the first position when the liquid sample is applied to the device; and
   (b) moving the second sub-assembly to the second position.

19. The method of claim 18 wherein (b) is performed after a determined time has elapsed since the application of the liquid sample to the device.

* * * * *

UNITED STATES PATENT AND TRADEMARK OFFICE
CERTIFICATE OF CORRECTION

PATENT NO.       : 7,611,669 B1                                                 Page 1 of 1
APPLICATION NO.  : 10/181620
DATED            : November 3, 2009
INVENTOR(S)      : Crisanti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 789 days.

Signed and Sealed this

Twelfth Day of October, 2010

David J. Kappos
*Director of the United States Patent and Trademark Office*